United States Patent [19]

Cassidy et al.

[11] 4,136,190
[45] Jan. 23, 1979

[54] 4,4-DIMETHYL-3,5-PYRROLIDINEDIONES

[75] Inventors: Frederick Cassidy, Harlow; Antony W. Lake, Saffron Walden, both of England

[73] Assignee: Beecham Group Limited, Great Britain

[21] Appl. No.: 732,989

[22] Filed: Oct. 15, 1976

[30] Foreign Application Priority Data

Oct. 25, 1975 [GB] United Kingdom .............. 43989/75
May 22, 1976 [GB] United Kingdom .............. 21279/76

[51] Int. Cl.$^2$ ..................... A61K 31/40; C07D 207/40
[52] U.S. Cl. .............................. 424/274; 260/326.44; 260/326.43
[58] Field of Search ...................... 260/326.44, 326.45, 260/326.43; 424/274

[56] References Cited

U.S. PATENT DOCUMENTS 3,975,399 8/1976 de Franco et al. ............. 260/326.43
4,003,911 1/1977 Scribner ......................... 260/326.44

Primary Examiner—Jose Tovar
Attorney, Agent, or Firm—Jacobs & Jacobs

[57] ABSTRACT

Compounds of formula (I):

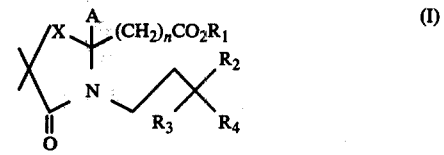

wherein: n is 4 to 8, X is CO, protected CO or CROH wherein R is hydrogen or $C_{1-4}$ alkyl and wherein the OH moiety may be protected; $R_1$ is hydrogen, or $CO_2R_1$ represents an ester group in which the $R_1$ moiety contains from 1 to 12 carbon atoms; $R_3$ is hydroxy or protected hydroxy; $R_2$ and $R_4$ are separately hydrogen, $C_{1-9}$ alkyl, $C_{5-8}$ cycloalkyl, $C_{5-8}$ cycloalkyl-$C_{1-6}$ alkyl, phenyl, phenyl $C_{1-6}$ alkyl, naphthyl, naphthyl $C_{1-6}$ alkyl, any of which phenyl or naphthyl moieties may be substituted by one or more halogen, trifluoromethyl, $C_{1-6}$ alkyl, $C_{1-6}$ alkoxy or nitro groups; or $R_2$ and $R_4$ taken with the carbon atoms to which they are joined represent $C_{5-8}$ cycloalkyl; A is hydrogen or a group $CO_2B$ wherein B is hydrogen, or $CO_2B$ represents an ester group in which the B moiety contains from 1 to 12 carbon atoms; or methyl; and salts thereof; have useful pharmacological properties including anti-gastric secretion, bronchodilator and platelet aggregration inhibition activities.

37 Claims, No Drawings

4,4-DIMETHYL-3,5-PYRROLIDINEDIONES

This invention relates to novel compounds having pharmacological activity, to processes for their preparation, to intermediates useful in that process and to pharmaceutical compositions containing them.

More specifically, this invention relates to novel 3,5-dione-4,4-dimethyl pyrrolidines and derivatives thereof in which the nitrogen atom is substituted by an aliphatic or aliphatic-aromatic group and the free α-carbon atom is substituted by an aliphatic group.

Natural prostaglandins and analogues thereof are known to possess a wide variety of pharmacological activities.

Offenlegungsschrift No: 2323193 discloses that pyrazolidine derivatives of the formula (I)':

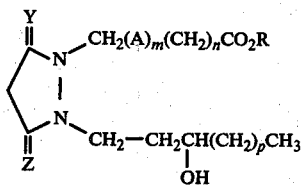

wherein A is CH=CH or C≡C; R is H, an alkali metal, an amine salt, or an ≯ 12C hydrocarbon or chlorohydrocarbon residue; m is 0 or 1; n is 0-6; p is 0-6; and Y and Z are 0 or $H_2$ except that Y and Z are not both 0; have similar biological properties to the prostaglandins or are antagonists of prostaglandins.

A paper by Bolliger and Muchowski (Tet. Letters, 1975, 2931) describes the preparation of 11-desoxy-8-azaprostaglandin $E_1$, but states only that one epimer thereof was more active in several biological assays than the other epimer.

Our copending U.S. patent application Ser. No. 632975 discloses that compounds of the formula (I)":

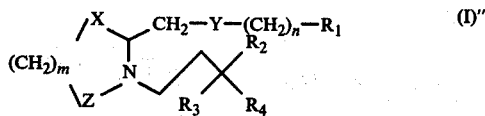

wherein:

X is CO, protected CO, CROH in which R is hydrogen or $C_{1-4}$ alkyl and in which the OH moiety may be protected; Y is $CH_2CH_2$ or CH=CH; Z is CO or $CH_2$; n is 1 to 8; m is 1, 2 or 3; $R_1$ is hydrogen, $CH_2OH$, $CH_2OH$ in which the OH moiety is protected $CO_2W$ wherein W is hydrogen or $CO_2W$ represents an ester group in which the ester moiety contains from 1 to 12 carbon atoms, or $CONH_2$; $R_2$ is hydrogen, $C_{1-4}$ alkyl, or taken together with $R_3$ and the carbon atom to which it is attached represents a carbonyl group; $R_3$ is hydrogen, hydroxy or protected hydroxy; $R_4$ is hydrogen or $C_{1-9}$ alkyl; and salts thereof; have useful pharmacological activity. This subject matter was first published in Belgium Patent No: 835989 on the 26th May 1976, a date later than the filing dates of the two UK Applications Nos: 43989/75 and 21279/76 from which priority has been claimed for the present invention.

A novel class of compounds having useful pharmacological activity has now been discovered, which compounds are structurally distinct from the prior art referred to above.

Accordingly, the present invention provides a compound of the formula (I):

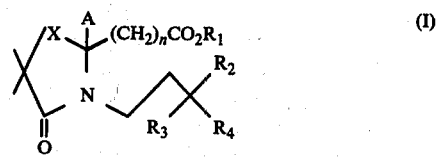

wherein:

n is 4 to 8;

X is CO, protected CO or CROH wherein R is hydrogen or $C_{1-4}$ alkyl and wherein the OH moiety may be protected;

$R_1$ is hydrogen, or $CO_2R_1$ represents an ester group in which the $R_1$ moiety contains from 1 to 12 carbon atoms;

$R_3$ is hydroxy or protected hydroxy;

$R_2$ and $R_4$ are separately hydrogen, $C_{1-9}$ alkyl, $C_{5-8}$ cycloalkyl, $C_{5-8}$ cycloalkyl-$C_{1-6}$ alkyl, phenyl, phenyl $C_{1-6}$ alkyl, naphthyl, naphthyl $C_{1-6}$ alkyl, any of which phenyl or naphthyl moieties may be substituted by one or more halogen, trifluoromethyl, $C_{1-6}$ alkyl, $C_{1-6}$ alkoxy or nitro groups; or $R_2$ and $R_4$ taken with the carbon atom to which they are joined represent $C_{5-8}$ cycloalkyl;

A is hydrogen or a group $CO_2B$ wherein B is hydrogen, or $CO_2B$ represents an ester group in which the B moiety contains from 1 to 12 carbon atoms; or methyl; and salts thereof.

Suitably n is 5, 6 or 7, preferably 6.

Suitable protected hydroxyl groups CROH and $R_3$ include readily hydrolysable groups such as acylated hydroxy groups in which the acyl moiety contains 1 to 4 carbon atoms, for example the acetoxy group; and hydroxy groups etherified by readily removable inert groups such as the benzyl or like groups. Preferably $R_3$ is hydroxyl and the hydroxy moiety in CROH is unprotected.

Examples of suitable groups X include CO, CHOH, $C(CH_3)OH$ and $C(C_2H_5)OH$. Preferably X is CO, CHOH or $C(CH_3)OH$, and most preferably CO.

X may also be a protected CO group. Suitable examples of such protected CO groups X include groups formed by conventional carbonyl addition and condensation reactions such as ketals, thioketals, hemithioketals, oximes, semicarbazones, hydrazones and the like. Of such groups often the ketal type derivatives will be most useful, for example when X is a group

$R_1$ is hydrogen or $CO_2R_1$ represents an ester group in which the $R_1$ moiety contains from 1 to 12 carbon atoms. Examples of $R_1$ include hydrogen, methyl, ethyl, propyl, butyl, phenyl, benzyl, toluyl and the like, while normally hydrogen or $C_{1-4}$ alkyl groups are preferred.

Suitable groups $R_4$ when $R_4$ is an alkyl group include $C_{4-9}$ alkyl groups. Such $C_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, $R_4$ may be a group $CH_2R_5$, $CH(CH_3)R_5$ or $C(CH_3)_2R_5$, wherein $R_5$ is a straight chain alkyl group such that the carbon content of the resultant group $R_4$ is 4 to 9.

In general preferred groups $R_4$ when $R_4$ is an alkyl group include straight chain pentyl, hexyl and heptyl groups. Of these, straight chain hexyl is often the most useful. Other preferred groups $R_4$ include groups $CH(CH_3)R_5$ and $C(CH_3)_2R_5$ wherein $R_5$ is straight chain butyl, pentyl and hexyl.

When $R_4$ is or contains a $C_{5-8}$ cycloalkyl moiety, the moiety is suitably a cyclohexyl moiety. Examples of suitable $C_{1-6}$ alkyl moieties when $R_4$ is a $C_{5-8}$ cycloalkyl-$C_{1-6}$ alkyl group include methyl, ethyl, propyl, butyl and amyl.

When $R_4$ is an aryl group as previously defined, suitable groups $R_4$ include phenyl, phenylmethyl, phenylethyl, phenyl n-propyl, phenyl n-butyl, naphthyl, naphthylmethyl, naphthylethyl, naphthyl n-propyl and naphthyl n-butyl, and such groups branched in the alkyl moiety by one or two methyl groups (at the same or different carbon atoms). These groups may be substituted in the phenyl or naphthyl moiety by normally one, two or three groups selected from those substituent groups listed herein before. Examples of suitable substituent groups include fluorine, chlorine and bromine atoms and $CF_3$, methyl, ethyl, n- and iso-propyl, methoxy and ethoxy, n- and iso-propoxy and nitro groups. Preferably the aryl moieties when substituted by such groups will be mono- or di-substituted.

Particularly suitable values for $R_2$ are hydrogen, $C_{1-4}$ alkyl and phenyl, for example, methyl, ethyl and phenyl. Of these groups, preferred groups include methyl and ethyl.

Otherwise $R_2$ can suitably represent groups such as those described above as suitable and preferred groups for $R_4$.

Also, $R_2$ and $R_4$ taken with the carbon atom to which they are joined can represent a $C_{5-8}$ cycloalkyl group, such as the cyclohexyl group.

A may be hydrogen or a group $CO_2B$. Suitable examples of B include hydrogen and methyl, ethyl, propyl, butyl, phenyl, benzyl, toluyl, and the like, while normally for B hydrogen or $C_{1-4}$ alkyl are preferred. While the groups B and $R_1$ may be different, it is normally preferred that they are both hydrogen or the same $C_{1-4}$ alkyl groups. In general the most useful compounds of this sort are those wherein A is hydrogen.

Another important group of compounds of the formula (I) are those wherein A is methyl.

The compounds of the formula (I) may form conventional acid salts when $R_1$ is hydrogen. Such salts include those with alkali and alkaline earth metals, suitably sodium and potassium, and ammonium and substituted ammonium salts.

A group of compounds within the compounds of the formula (I) as defined are those wherein X is CO, or CROH wherein R is hydrogen or $C_{1-4}$ alkyl and wherein the OH moiety may be protected; $R_2$ is hydrogen, $C_{1-4}$ alkyl or phenyl; $R_4$ is hydrogen, $C_{1-9}$ alkyl, phenyl, phenyl $C_{1-4}$ alkyl, naphthyl, naphthyl $C_{1-4}$ alkyl, any of which phenyl or naphthyl moieties may be substituted by one or more halogen, trifluoromethyl, $C_{1-6}$ alkyl, $C_{1-6}$ alkoxy or nitro groups; and A is hydrogen or a group $CO_2B$ wherein B is hydrogen, or $CO_2B$ represents an ester group in which the B moiety contains from 1 to 12 carbon atoms; and salts thereof.

One particularly suitable sub-group of compounds within such compounds of formula (I) include those of formula (II):

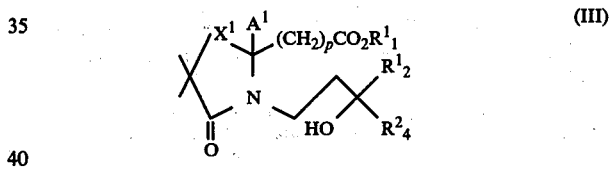

wherein:
p is 6 or 8;
$X^1$ is CO, CHOH or $C(CH_3)OH$;
$R^1_1$ is hydrogen or $C_{1-4}$ alkyl;
$R^1_2$ is hydrogen, methyl or ethyl;
$R^1_4$ is hydrogen or $C_{1-9}$ alkyl; and
$A^1$ is hydrogen or a group $CO_2R^1_1$; and salts thereof.

In formula (II), p is most suitably 6, $X^1$ is most suitably CO, $R^1_2$ is most suitably methyl or ethyl and $A^1$ is most suitably hydrogen.

While $R^1_4$ may be hydrogen or a $C_{1-9}$ alkyl group, it is normally a $C_{4-9}$ alkyl group. In such cases suitable and preferred straight chain and branched groups $R^1_4$ include those previously described as suitable and preferred for the group $R_4$ when $R_4$ is a $C_{4-9}$ alkyl group. Such preferred groups $R^1_4$ include straight chain pentyl, hexyl and heptyl, and of these normally the most useful is straight chain hexyl. Other preferred groups $R^1_4$ include $CH(CH_3)R^1_5$ and $C(CH_3)_2R^1_5$ wherein $R^1_5$ is straight chain butyl, pentyl or hexyl.

A second sub-group of interest within such compounds of formula (I) includes compounds of the formula (III):

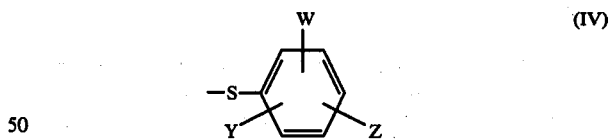

wherein:
p, $X^1$, $R^1_1$, $R^1_2$ and $A^1$ are as defined in formula (II); and $R^2_4$ is a group of formula (IV):

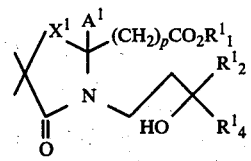

wherein S is a bond, or a $C_{1-6}$ alkylene group which may be straight chain or branched by one or two methyl groups at the same or different carbon atoms; and W, Y and Z are each hydrogen or fluorine, chlorine or bromine atoms, or $CF_3$, methyl, ethyl, n- or iso-propyl, methoxy, ethoxy, n- or iso-propoxy or nitro groups; and salts thereof.

Often S will be a group $-(CH_2)_q-$ wherein q is 0 to 4.

In formula (III) p is most suitably 6, $X^1$ is most suitably CO, $R^1_2$ is most suitably methyl or ethyl, and $A^1$ is most suitably hydrogen. Also, W is most suitably hydrogen.

A third sub-group of compounds within such compounds of formula (I) of interest include those of formula (V):

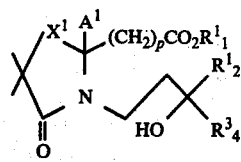 (V)

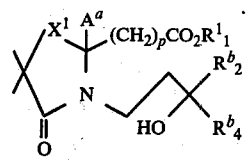 (IX)

wherein p, $R^1_1$, $R^1_2$ and $A^1$ are as defined in formula (II), and $R^3_4$ is a group of formula (VI):

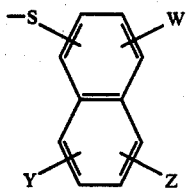 (VI)

wherein S, W, Y and Z are as defined in formula (IV); and salts thereof.

Often S will be a group —$(CH_2)_q$— wherein q is 0 to 4.

In formula (V) we prefer that p is 6. Most suitably $X^1$ is CO, $R^1_2$ is methyl or ethyl, and $A^1$ is hydrogen.

The sub-groups of formula (II), (III) and (V) all involve compounds wherein $R^1_2$ is hydrogen, methyl or ethyl. When $R^1_2$ is phenyl, particularly interesting compounds within the formula (I) include those of the formula (II), (III) and (V) as hereinbefore defined but wherein $R^1_2$ is phenyl.

A further group of compounds of interest are those of formula (II), (III) or (V) as defined hereinbefore but wherein $A^1$ is methyl.

A fourth sub-group of compounds within formula (I) of interest include those of formula (VII):

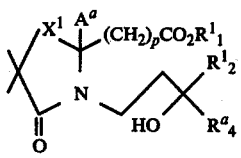 (VII)

wherein:
p, $X^1$, $R^1_1$ and $R^1_2$ are as defined in formula (II);
$A^a$ is hydrogen, or a group $CO_2R^1_1$, or methyl;
$R^a_4$ is a group of formula (VIII):

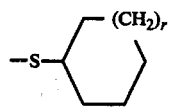 (VIII)

wherein S is as defined in formula (IV) and r is 0 to 3; and salts thereof.

Often S will be a group - $(CH_2)_q$ wherein q is 0 to 6.

In formula (VII) we prefer that p is 6. Most suitably $X^1$ is CO, $R^1_2$ is methyl or ethyl, and $A^a$ is hydrogen or methyl.

A fifth sub-group of compounds within formula (I) of interest include those of formula (IX):

wherein:
p, $X^1$, $R^1$ and $A^a$ are as defined in formula (VII); $R^b_2$ and $R^b_4$ are separately $C_{5-9}$ alkyl or groups of formula (IV), (VI) or (VIII) as defined; or $R^b_2$ and $R^b_4$ taken together with the carbon atom to which they are joined represent $C_{5-8}$ cycloalkyl; and salts thereof.

In formula (IX) we prefer that p is 6. Most suitably $X^1$ is CO, and $A^a$ is hydrogen or methyl.

Compounds as defined in the aforesaid sub-groups, but wherein $X^1$ is a protected CO group, are also of particular utility.

The invention also provides a process for the preparation of a compound of the formula (I) wherein A is hydrogen or $CO_2B$ which process comprises the methylation of a compound of the formula (X):

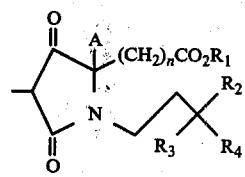 (X)

wherein N, $R_1$, $R_2$, $R_3$ and $R_4$ are as defined in formula (I), and A is hydrogen or $CO_2B$ to yield a compound of the formula (I) wherein X is CO; and thereafter if desired protecting X, or converting X in the thus formed compound to CROH by reduction when R is hydrogen or by reaction with a $C_{1-4}$ alkyl Grignard reagent or $C_{1-4}$ alkyl metallic complex when R is $C_{1-4}$ alkyl, and then optionally protecting the CROH hydroxy moiety.

The methylation is conveniently carried out by reacting the chosen compound of the formula (X) with a strong base and a source of $CH_3^+$ ions in an inert solvent. Suitable strong bases include sodium hydride, suitable sources of $CH_3^+$ ions include the methyl halides such as methyl iodide, and suitable inert solvents include benzene and the like.

The invention also provides a process for the preparation of a compound of the formula (I) wherein A is methyl, which process comprises methylating a compound of formula (I) wherein X is CO and A is hydrogen; and thereafter if desired protecting X, or converting X in the thus formed compound to CROH by reduction when R is hydrogen or by reaction with a $C_{1-4}$ alkyl Grignard reagent or $C_{1-4}$ alkyl metallic complex when R is $C_{1-4}$ alkyl, and then optionally protecting the CROH hydroxy moiety.

The methylation is suitably carried out as for a compound of formula (X) as described above but in a more polar solvent such as dimethyl formamide.

After these reaction $R_1$ may be varied by conventional de-esterification and/or esterification reactions. Similarly protected CROH and $R_3$ hydroxy moieties may be deprotected by conventional methods. For example, when $R_3$ is a benzyloxy group, the benzyl group may readily be removed by hydrogenolysis. Thus it may be seen that 'protected hydroxy' compounds of the formula (I) are useful intermediates in the preparation of the corresponding 'free hydroxy' compounds of the formula (I).

The conversion of a compound of the formula (I) wherein X is CO to the corresponding compound wherein X is protected CO may be carried out under conventional reaction conditions, for example, for carbonyl addition and condensation reactions.

The conversion of a compound of the formula (I) wherein X is CO to the corresponding compound wherein X is CHOH may be carried out by conventional methods for reducing a ketone to an alcohol, for example by sodium borohydride reduction.

The conversion of a compound of the formula (I) wherein X is CO to the corresponding compound wherein X is CROH in which R is $C_{1-4}$ alkyl may be carried out by conventional Grignard or alkyl metal, (suitably alkyl lithium) reactions.

When $R_1$ is hydrogen, salts of compounds of the formula (I) may be prepared in conventional manner, for example, by reacting the chosen compound of the formula (I) with the required base.

The preparation of the intermediates for use in the preparation of the compounds of the formula (I) will now be discussed.

When A is hydrogen in the compound of the formula (X), then this compound of the formula (X) may be prepared by the mono-methylation of a compound of formula (XI):

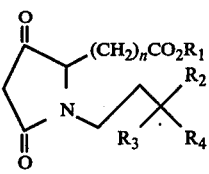
(XI)

wherein n, $R_1$, $R_2$, $R_3$ and $R_4$ are as defined in formula (X). This monomethylation will be carried out by conventional methods such as those described above for the monomethylation of a compound of the formula (X). After the monomethylation it will often be necessary to separate the desired monomethyl compound of the formula (X) from biproducts formed in the reaction, and this may be done in conventional manner.

It will however normally be preferred to generate the required compound of the formula (I) wherein A is hydrogen or methyl directly from the corresponding compound of the formula (XI) by reacting this compound of the formula (XI) with excess methylating agent under the appropriate conditions.

When A is a group $CO_2B$ as defined in the compound of the formula (X) then this compound of the formula (X) may be prepared by a process which comprises cyclising a compound of the formula (XII):

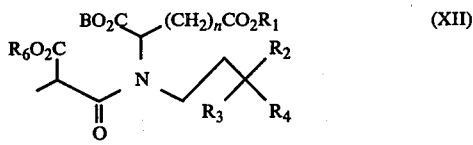
(XII)

wherein n, $R_1$, $R_2$, $R_3$, $R_4$ and $CO_2B$ are as defined in formula (I), and $R_6$ is a $C_{1-12}$ group such that $CO_2R_6$ is an ester group.

Most suitably $R_6$ is a $C_{1-4}$ alkyl group or a benzyl group or the like, and the groups $R_6$, B and $R_1$ are the same $C_{1-4}$ alkyl group such as the methyl or ethyl groups. Generally, the cyclisation reaction takes place in a dry organic solvent using a strong base such as sodium hydride or sodium ethoxide (or other $^-OR_6$ or $^-OB$ group) to bring about the initial proton abstraction from the methine group. It has been found that sodium ethoxide in benzene or potassium t-butoxide in toluene, benzene or hexamethylphosphoramide give good results. Often in this cyclisation reaction a mixture of products will be obtained, and the required compound of the formula (X) wherein A is $CO_2B$ will be separated therefrom by conventional methods.

The compounds of the formula (I) wherein A is $CO_2B$ as defined may also be prepared directly by a process which comprises cyclising a compound of the formula (XIII):

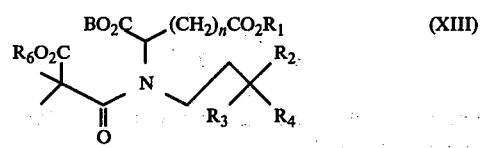
(XIII)

wherein n, $R_1$, $R_2$, $R_3$, $R_4$, $CO_2B$ and $CO_2R_6$ are as defined in formula (XII) to yield a compound of the formula (I) wherein X is CO; and thereafter if desired protecting X, or converting X in the thus formed compound to CROH by reduction when R is hydrogen or by reaction with a $C_{1-4}$ alkyl Grignard reagent or $C_{1-4}$ alkyl metallic complex when R is $C_{1-4}$ alkyl, and then optionally protecting the CROH hydroxy moiety.

The cyclisation is carried out as described for the cyclisation of a compound of formula (XII) with the difference that the required compound of the formula (I) formed in the cyclisation reaction is normally the only major product of the reaction. For this reaction it is often preferred to prepare compounds of the formula (I) wherein A is $CO_2B$ as defined by this cyclisation process rather than by the cyclisation/methylation process described earlier.

After the compound of the formula (XIII) has been cyclised, the optional steps thereafter to vary X in the resultant compound of the formula (I) are carried out in the manner described earlier in the specification in relation to the monomethylation of compound (X).

The compounds of the formula (X), (XI), (XII) and (XIII) are useful intermediates in the preparation of the compounds of the formula (I), and as such form an important aspect of this invention.

The compound of the formula (XI) may be prepared by a process which comprises decarboxylating a compound of the formula (XIV):

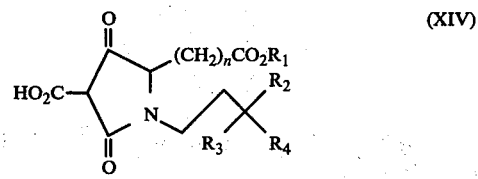
(XIV)

wherein n, $R_1$, $R_2$, $R_3$ and $R_4$ are as defined in formula (I).

The decarboxylation reaction may be brought about under basic, acid or neutral conditions in conventional manner. For example the reaction may conveniently be effected by heating the chosen compound of the formula (XIV) in a suitable solvent such as toluene or xylene.

It is frequently convenient however to generate the compound of the formula (XI) directly from an ester of the formula (XV), and often this will in fact be the preferred route:

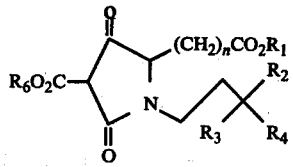
(XV)

wherein $CO_2R_6$ is a conventional ester group as defined. In such a case $R_6$ is preferably a benzyl group or a $C_{1-4}$ alkyl group such as methyl or ethyl or the like. It has been found that often it is sufficient to bring about de-esterification and subsequent decarboxylation in the chosen compound of the formula (XV) simply by leaving the compound of the formula (XV) standing in an inert solvent, for example over-night. Otherwise the desired de-esterification and decarboxylation in the chosen compound of the formula (XV) can be brought about by treatment with lithium iodide dihydrate and collidine in anhydrous solvents, for example, or by heating the chosen compound alone or preferably in a high boiling solvent such as toluene or xylene.

It will be appreciated that compounds of the formulae (XIV) and (XV) useful intermediates and as such form a useful aspect of this invention.

The compounds of the formula (XV) may be prepared by a process which comprises the ring closure of a compound of the formula (XVI):

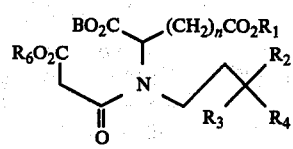
(XVI)

in an analogous manner to the ring closure of a compound of the formula (XIII) as hereinbefore described.

The compound of the formula (XVI) is again a useful intermediate, and as such part of the invention.

In the above described processes, the group $CO_2R_1$ in the appropriate intermediates will normally represent an ester group, and if acids of the formula (I) (wherein $R_1$ is hydrogen) are required they will be obtained by de-esterification of the corresponding compound of the formula (I) wherein $CO_2R_1$ is an ester group. Usually the group $CO_2B$ in the intermediates will be the same ester group as $CO_2R_1$, and for the sake of convenience the ester group $CO_2R_6$ will also normally be the same ester group as $CO_2R_1$. The ester groups $CO_2R_1/B/R_6$ are suitably $C_{1-4}$ alkyl esters, such as methyl or ethyl esters.

It will be seen that the intermediates of the formula (XVI), (XII) and (XIII) may be represented by the common formula (XVII).

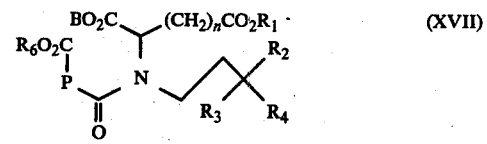
(XVII)

wherein P is —$CH_2$— (to give compounds (XVI)), or —$CH(CH_3)$— (to give compounds (XII)), or —$C(CH_3)_2$— (to give compounds XIII)).

These compounds of the formula (XVII) may be prepared by the esterification of a corresponding acid or by the reaction of a compound of the formula (XVIII):

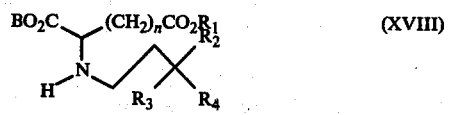
(XVIII)

with a reactive acylating derivative of an acid of the formula (XIX):

$$HO_2C - P - CO_2H \qquad (XIX)$$

or an ester thereof.

Suitable reactive acylating derivatives include (a) compounds of the formula (XX):

$$R_6O_2C - P - CO-Z \qquad (XX)$$

where Z is a readily displaceable group such as Cl, Br, $OSO_2CH_3$, $OSO_2C_6H_4CH_3$, $OCO(CH_2)_mCO_2R_6$ or like, (b) compounds of the formula (XX) wherein Z is OH in the presence of dicyclohexyl carbodiimide as a condensing agent.

The reaction of the compound (XVIII) with the compound (XIX) or (XX) occurs under conventional acylation conditions.

The novel substituted amino acids (XVIII) are highly useful intermediates and form an important aspect of the present invention.

The compounds (XVIII) may be prepared by the reaction of an amine of the formula (XXI):

$$H_2N - CH_2CH_2CR_2R_3R_4 \qquad (XXI)$$

with a compound of the formula (XXII):

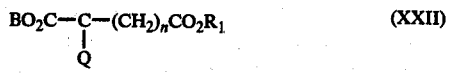
(XXII)

where Q is a group readily displaceable by an electron rich group.

Suitable groups Q include I, Br, Cl, $O.SO_2CH_3$, $O.SO_2C_6H_4CH_3$ and other conventional groups.

The displacement reaction occurs under conventional reaction conditions, for example, in an alcoholic solvent in the presence of anhydrous $Na_2CO_3$ or pyridine.

When $R_2$ is hydrogen or lower alkyl then the amine (XXI) can be prepared by conventional methods. However when $R_2$ and $R_4$ are higher alkyl or cyclic groups as defined in formula (I), then the amine is best prepared by the following reaction scheme, or a scheme chemically analogous thereto:

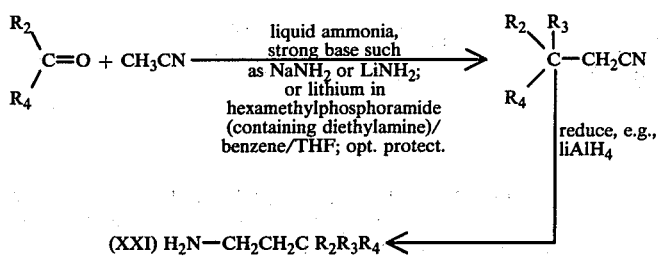

(XXI) $H_2N-CH_2CH_2C\ R_2R_3R_4$

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

Compounds within the formula (I) have useful pharmacological activity. For example compounds within the formula (I) have anti-gastric secretion activity, cardiovascular activity e.g. anti-hypertensive activity, platelet aggregration inhibition activity, affect the respiratory tract e.g. bronchodilator activity, and have anti-fertility and smooth muscle activity.

In general it may be said that compounds within the formula (I) have a range of pharmacological activities similar to those shown by the natural prostaglandins, but that these activities tend to be rather more selective.

The invention therefore also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as a preference in a particular area of therapy for a particular mode of administration.

The compositions may be in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; filler for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. The compounds of the formula (I) may also if desired be incorporated in a food-stuff, for example in the form of a biscuit.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It has been found that a number of the compounds of the formula (I) are potent inhibitors of gastric secretion, and thus have commercial utility as anti-ulcer agents. In treatment of this nature, the composition containing the formula (I) will preferably be formulated in a manner to allow oral administration. Normally 0.01 mg/kg to 500 mg/kg per day, most suitably 0.1 to 100 mg/kg per day, of the compound of the formula (I) in composition form will be administered in such treatment.

Also a number of compounds of the formula (I) have particularly useful activity on the respiratory tract, and thus find utility as for example bronchodilators. Normally compositions containing such compounds of the formula (I) will be formulated for aerosol or oral administration, or as a microfine powder for insufflation, and the treatment will comprise the administration of from 0.001 mg/kg to 100 mg/kg per day of the compound in composition form.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or propylaxis of disorders in human beings which comprises the administration to the sufferer of an effective amount of a compound of the formula (I).

The following Examples illustrate the preparation of compounds of the formula (I) and their pharmacological properties.

EXAMPLE 1

4,4-Dimethyl-2-(6'-ethoxycarbonyl-n-hexyl)-1-(3''-hydroxy-3''-methyl-n-nonyl)-pyrrolidin-3,5-dione Sodium hydride (2.91 g, 80% dispersion) was washed with hexane, blown dry under nitrogen and suspended in dry benzene (50 ml). A solution of 2-(6'-ethoxycarbonyl-n-hexyl)-1-(3''-hydroxy-3''-methyl-n-nonyl)-pyrrolidin-3,5-dione (10.0 g) in dry benzene (60 ml) was added and the mixture was stirred at room temperature under nitrogen for 1 hour.

The mixture was heated to 70° and a solution of methyl iodide (37.8 g) in dry benzene (50 ml) was added dropwise. The mixture was heated at 70° for 2 hours.

The reaction mixture was cooled and glacial acetic acid (3.26 ml) added. The mixture was filtered and the filtrate evaporated in vacuo to give a yellow oil. The product was purified by column chromatography to give 4,4-dimethyl-2-(6'-ethoxycarbonyl-n-hexyl)-1-(3''-hydroxy-3''-methyl-n-nonyl)-pyrrolidin-3,5-dione as a yellow oil (3.49 g, 33% yield).

I.R. spectrum - carbonyl absorptions at 1760 cm$^{-1}$, 1730 cm$^{-1}$ and 1680 cm$^{-1}$. broad OH absorption at 3450 cm$^{-1}$.

The compounds shown in Table 1 were similarly prepared:

Table 1

| Compound | n | $R_1$ | $R_2$ | $R_4$ |
|---|---|---|---|---|
| 1 | 6 | $CH_3$ | $CH_3$ | $C_6H_{13}$ |
| 2 | 6 | $C_2H_5$ | $CH_3$ | $(CH_2)_2C_6H_5$ |
| 3 | 5 | $C_2H_5$ | $CH_3$ | $C_6H_{13}$ |
| 4 | 6 | $C_2H_5$ | $CH_3$ | $C_8H_{17}$ |
| 5 | 6 | $C_2H_5$ | $CH_3$ | $C_4H_9$ |
| 6 | 6 | $C_2H_5$ | $C_2H_5$ | $C_6H_{13}$ |
| 7 | 6 | $C_2H_5$ | $CH_3$ | $(CH_2)_3C_6H_5$ |
| 8 | 6 | n-$C_4H_9$ | $CH_3$ | $C_6H_{13}$ |
| 9 | 6 | $C_2H_5$ | $CH_3$ | $C_5H_{11}$ |
| 10 | 6 | $C_2H_5$ | $CH_3$ | $C_7H_{15}$ |
| 11 | 6 | $C(CH_3)_3$ | $CH_3$ | $C_6H_{13}$ |
| 12 | 6 | $C_2H_5$ | $CH_3$ | $CH_2C_6H_5$ |
| 13 | 6 | $C_2H_5$ | $CH_3$ | $C_6H_5$ |
| 14 | 6 | $C_2H_5$ | $CH_3$ | $CH(CH_3)C_6H_5$ |
| 15 | 6 | $C_2H_5$ | $C_6H_5$ | $C_5H_{11}$ |
| 16 | 6 | $C_2H_5$ | $CH_3$ | $(CH_2)_3$—C$_6$H$_4$—OCH$_3$ |

In each case the I.R. spectrum showed carbonyl absorptions at 1760 cm$^{-1}$, 1730 cm$^{-1}$ and 1680 cm$^{-1}$ and a broad OH absorption at 3400–3500 cm$^{-1}$.

EXAMPLE 2

4,4-Dimethyl-2-(6'-ethoxycarbonyl-n-hexyl)-3-hydroxyl-1-(3''-hydroxy-3''-methyl-n-nonyl)-pyrrolidin-5-one Sodium borohydride (125 mg) was added portionwise to a solution of 4,4-dimethyl-2-(6'-ethoxycarbonyl-n-hexyl)-1-(3''-hydroxy-3''-methyl-n-nonyl)-pyrrolidin-3,5-dione (980 mg) in dry ethanol (25 ml). The mixture was stirred at room temperature for 2 hours.

The solvent was evaporated in vacuo and the residue was taken up in ether. The ethereal solution was washed with very dilute hydrochloric acid and with water, dried over magnesium sulphate and evaporated in vacuo to give a colourless oil. The product was purified by column chromatography to give 4,4-dimethyl-2-(6'-ethoxycarbonyl-n-hexyl)-3-hydroxy-1-(3''-hydroxy-3''-methyl-n-nonyl)-pyrrolidin-5-one as a colourless oil (559 mg, 57% yield).

I.R. spectrum — carbonyl absorptions at 1735 cm$^{-1}$ and 1665 cm$^{-1}$. strong, broad OH absorption at 3450 cm$^{-1}$.

4,4-Dimethyl-2-(6'-ethoxycarbonyl-n-hexyl)-3-hydroxy-1-(3''-hydroxy-3''-ethyl-n-nonyl)pyrrolidin-5-one was similarly prepared.

I.R. spectrum — carbonyl absorption at 1720 cm$^{-1}$ and 1660 cm$^{-1}$. broad OH absorption at 3450 cm$^{-1}$.

EXAMPLE 3

2-(6'-Carboxy-n-hexyl)-4,4-dimethyl-1-(3''-hydroxy-3''-methyl-n-nonyl)pyrrolidin-3,5-dione A 10% solution of potassium carbonate (6.0 ml) was added to a solution of 4,4-dimethyl-2-(6'-ethoxycarbonyl-n-hexyl)-1-(3''-hydroxy-3''-methyl-n-nonyl)-pyrrolidin-3,5-dione (900 mg) in ethanol (20 ml). The mixture was gently refluxed for 24 hours.

The solvent was evaporated in vacuo and the residue was taken up in water. The aqueous solution was extracted with ether and acidified with dilute hydrochloric acid. The acid solution was extracted with ether and this ethereal solution was washed with water, dried over magnesium sulphate and evaporated in vacuo to give a colourless oil. The product was purified by column chromatography to give 2-(6'-carboxy-n-hexyl)-4,4-dimethyl-1-(3''-hydroxy-3''-methyl-n-nonyl)-pyrrolidin-3,5-dione as a colourless oil (586mg 70% yield.

I.R. spectrum — carbonyl absorptions at 1760 cm$^{-1}$, 1725 cm$^{-1}$ and 1670 cm$^{-1}$. broad OH absorption around 3400 cm$^{-1}$.

EXAMPLE 4

Diethyl-2-(N-3'-benzyloxy-n-nonyl)-aminoazelate

A solution of diethyl 2-bromoazelate (114 g) in dry ethanol (200 ml) was added dropwise to a refluxing solution of 3-benzyloxy-n-nonylamine (80 g) in dry ethanol (500 ml) containing a suspension of anhydrous sodium carbonate (41 g). The mixture was refluxed with stirring for 12 hours.

The reaction mixture was filtered and the filtrate evaporated in vacuo. The residue was taken up in ether (500 ml) and the ethereal solution was washed with saturated brine until neutral, dried over magnesium sulphate and evaporated in vacuo to give diethyl 2-(N-3'-benzyloxy-n-nonyl)-aminoazelate as a yellow oil (164 g).

Analysis: $C_{29}H_{49}NO_5$ requires: C, 70.84%; H, 10.04%; N, 2.85%. Found: C, 71.20%; H, 10.14%; N, 2.74%.

EXAMPLE 5

Diethyl 2-[N-(3'-benzyloxy-n-nonyl)-N-(2',2'-dimethyl-ethoxycarbonyl-acetyl)]-aminoazelate Thionyl chloride (2.35 ml) was added dropwise to a solution of monoethyl 2,2-dimethylmalonate (4.71 g) in dry benzene (40 ml) and the mixture was refluxed for 2 hours.

The resulting solution of 2-ethoxycarbonyl-2,2-dimethyl-ethanoyl chloride was added dropwise to a solution of diethyl 2-(N-3'-benzyloxy-n-nonyl)-aminoazelate (7.05 g) in dry benzene (40 ml) containing a suspension of anhydrous sodium carbonate (18 g). The mixture was refluxed overnight with stirring.

The reaction mixture was filtered and the filtrate evaporated in vacuo. The residue was taken up in ether and the ethereal solution was washed with dilute hydrochloric acid, sodium bicarbonate and with water, dried over magnesium sulphate and evaporated in vacuo to give a brown oil. The product was purified by column chromatography to give diethyl 2-[N-(3'-benzyloxy-n-nonyl-N-(2'',2''-dimethyl-ethoxycarbonyl-acetyl)]-aminoazelate as a yellow oil (4.37 g, 48% yield).

I.R. spectrum — carbonyl absorptions at 1720 $cm^{-1}$ and 1640 $cm^{-1}$.

NMR spectrum — 5 proton singlet at 2.74$\tau$ ($C_6\underline{H}_5CH_2$); 2 proton singlet at 5.53$\tau$ ($C_6H_5C\underline{H}_2$); 2 proton quartets at 5.87$\tau$ and 5.92$\tau$, J=12 cps ($CO_2C\underline{H}_2CH_3$).

EXAMPLE 6

N-(3'-Benzyloxy-n-nonyl)-4,4-dimethyl-2-ethoxycarbonyl-2-(6''-ethoxycarbonyl-n-hexyl)-pyrrolidin-3,5-dione Potassium tert-butoxide (445 mg) was added in small portions over a period of 1 hour to a refluxing solution of diethyl 2-[N-(3'-benzyloxy-n-nonyl)-N-(2'',2''-dimethyl-ethoxycarbonylacetyl)]-aminoazelate (2.3 g) in dry toluene (45 ml). The mixture was refluxed with stirring under nitrogen for a further 45 minutes.

The solvent was evaporated in vacuo and the residue taken up in ether. The ethereal solution was washed with dilute hydrochloride acid, sodium carbonate solution and with water, dired over magnesium sulphate and evaporated in vacuo to give a yellow oil (1.38 g).

The crude product was combined with that from a similar experiment (2.13 g total) and purified by column chromatography to give N-(3'-benzyloxy-n-nonyl)-4,4-dimethyl-2-ethoxycarbonyl-2-(6''-ethoxycarbonyl-n-hexyl)-pyrrolidin-3,5-dione as an almost colourless oil (1.03 g).

I.R. spectrum — carbonyl absorptions at 1760 $cm^{-1}$, 1730 $cm^{-1}$ and 1690 $cm^{-1}$.

EXAMPLE 7

4,4-Dimethyl-2-ethoxycarbonyl-2-(6'-ethoxycarbonyl-n-hexyl)-N-(3''-hydroxy-n-nonyl)-pyrrolidin-3,5-dione 10% Pd/C (220 mg) was added to a solution of N-(3'-benzyloxy-n-nonyl)-4,4-dimethyl-2-ethoxycarbonyl-2-(6''-ethoxycarbonyl-n-hexyl)-pyrrolidin-3,5-dione (450 mg) in ethanol (50 ml). The mixture was hydrogenated at 50 psi and 50° overnight.

The catalyst was filtered off and the filtrate evaporated in vacuo to give a colourless oil (390 mg).

The crude product was combined with that from a similar experiment (799 mg) total. Column chromatography of this material allowed the two diastereoisomers of 4,4-dimethyl-2-ethoxycarbonyl-2-(6'-ethoxycarbonyl-n-hexyl)-N-(3''-hydroxy-n-nonyl)-pyrrolidin-3,5-dione to be largely separated as pale yellow oils (350 mg and 235 mg respectively).

Both diastereoisomers gave carbonyl absorptions at 1760 $cm^{-1}$, 1730 $cm^{-1}$ and 1685 $cm^{-1}$ and a broad OH absorption around 3400 $cm^{-1}$ in the I.R. spectrum.

EXAMPLE 8

1-(3'-Hydroxy-3'-methyl-n-nonyl)-2-(6''-methoxycarbonyl-n-hexyl)-2,4,4-trimethyl-pyrrolidin-3,5-dione A solution of 1-(3'-hydroxy-3'-methyl-n-nonyl)-2-(6''-methoxycarbonyl-n-hexyl)-pyrrolidin-3,5-dione (2.1 g) in dry dimethylformamide (10 ml) was added to a slurry of sodium hydride (640 mg, 80% dispersion) in dry benzene (10 ml) and dry dimethylformamide (10 ml). The mixture was stirred for 2 hours under nitrogen at room temperature.

A solution of methyl iodide (5 g) in dry dimethylformamide (5 ml) was run in dropwise and stirring was continued for 2 hours. Methyl iodide (5 g) was added and the mixture stirred for a further hour.

A few drops of glacial acetic acid were added and the solvent was removed in vacuo. The residue was taken up in ether and the ethereal solution was washed with water, dried over magnesium sulphate and evaporated to give a yellow oil. The product was purified by column chromatography to give 1-(3'-hydroxy-3'-methyl-n-nonyl)-2-(6''-methoxycarbonyl-n-hexyl)-2,4,4-trimethyl-pyrrolidin-3,5-dione as a yellow oil (453 mg, 20% yield).

Analysis: $C_{25}H_{45}NO_5$ requires: C, 68.30%; H, 10.32%; N, 3.19%. Found: C, 67.95%; H, 10.07%; N, 3.30%.

EXAMPLE 9

2-(6'-Carboxy-n-hexyl)-1-(3''-hydroxy-3''-methyl-n-nonyl)-2,4,4-trimethyl-pyrrolidin-3,5-dione A 10% solution of potassium carbonate (10 ml) was added to a solution of 1-(3'-hydroxy-3'-methyl-n-nonyl)-2-(6''-methoxycarbonyl-n-hexyl)-2,4,4-trimethyl-pyrrolidin-3,5-dione (1.35 g) in ethanol (25 ml). The mixture was gently refluxed for 24 hours.

The solvent was evaporated in vacuo and the residue was taken up in water. The aqueous solution was extracted with ether and acidified with dilute hydrochloric acid. The acid solution was extracted with ether and this ethereal solution was washed with water, dried over magnesium sulphate and evaporated in vacuo to give a thick, pale yellow oil. The product was purified by column chromatography to give 2-(6'-carboxy-n-hexyl)-1-(3''-hydroxy-3''-methyl-n-nonyl)-2,4,4-trimethyl-pyrrolidin-3,5-dione as a colourless oil (646 mg, 51% yield).

I.R. spectrum — carbonyl absorptions at 1760 $cm^{-1}$, 1720 $cm^{-1}$ and 1665 $cm^{-1}$. broad OH absorption around 3400 $cm^{-1}$.

PHARMACOLOGICAL DATA

Anti-secretory activity

The anti-secretory activity of the compounds was determined by their inhibition of pentagastrin-stimulated gastric acid secretion in the perfused rat stomach preparation (Ghosh and Schild preparation).

4,4-Dimethyl-2-(6'-ethoxycarbonyl-n-hexyl)-1-(3''-hydroxy-3''-methyl-n-nonyl)-pyrrolidin-3,5-dione inhibited acid secretion at 500 μg/kg, intravenously.

Bronchodilation activity

The compounds were examined for their ability to inhibit 5-hydroxytryptamine-induced bronchoconstriction in the anaesthetised, artificially respired guinea pig (Konzett-Rossler preparation).

4,4-Dimethyl-2-(6'-ethoxycarbonyl-n-hexyl)-1-(3''-hydroxy-3''-methyl-n-nonyl)-pyrrolidin-3,5-dione inhibited bronchoconstriction with an $IC_{50}$ of approximately 10 μg/kg, intravenously.

The compounds were examined for their ability to protect conscious guinea pigs from an aerosol administered histamine challenge. The compounds were given 30 minutes before the animals were challenged with a continuous aerosol of histamine.

2-(6'-Carboxy-n-hexyl)-4,4-dimethyl-1-(3''-hydroxy-3''-methyl-n-nonyl)-pyrrolidin-3,5-dione significantly prolonged the time taken to elicit a pre-convulsive cough in test animals compared with control animals when given at 2.5 mg/kg, intra-peritoneally, or when given at 10 mg/kg orally.

Toxicity

No toxic symptoms were observed when 4,4-dimethyl-2-(6'-ethoxycarbonyl-n-hexyl)-1-(3''-hydroxy-3''-methyl-n-nonyl)-pyrrolidin-3,5-dione was dosed up to 900 mg/kg, subcutaneously, in mice.

What we claim is:

1. A compound of the formula:

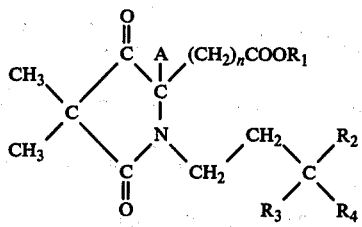

wherein
n is an integer having a value of from 4 to 8;
$R_1$ is hydrogen, or $CO_2R_1$ is an ester group in which $R_1$ contains from 1 to 12 carbon atoms;
$R_3$ is hydroxy alkanoyloxy of 1 to 4 carbon atoms or benzyloxy;
each of $R_2$ and $R_4$ when taken separately is hydrogen, alkyl of 1 to 9 carbon atoms, cycloalkyl of 5 to 8 carbon atoms, cycloalkyl-alkyl of 5 to 8 carbon atoms in the cycloalkyl moiety and 1 to 6 carbon atoms in the alkyl moiety, phenyl-alkyl of 1 to 6 carbon atoms in the alkyl moiety, naphthyl, naphthyl-alkyl of 1 to 6 carbon atoms in the alkyl moiety, said phenyl and naphthyl groups being unsubstituted or substituted by one or more members selected from the group consisting of halogen, trifluoromethyl, alkyl of 1 to 6 carbon atoms, alkoxy of 1 to 6 carbon atoms and nitro; or $R_2$ and $R_4$ when taken with the carbon atom to which they are joined are cycloalkyl of 5 to 8 carbon atoms;
A is hydrogen or methyl;
or an alkali metal, alkaline earth metal, ammonium or substituted ammonium salt of said compound in which $R_1$ is hydrogen.

2. A compound according to claim 1 wherein $R_2$ is hydrogen, alkyl of 1 to 4 carbon atoms or phenyl;
$R_4$ is hydrogen, alkyl of 1 to 9 carbon atoms, phenyl, phenylalkyl wherein alkyl has 1 to 4 carbon atoms, naphthyl, naphthylalkyl wherein alkyl has 1 to 4 carbon atoms, any of said phenyl or naphthyl groups being unsubstituted or substituted by one or more members selected from the group consisting of halo, trifluoromethyl, alkyl of 1 to 6 carbon atoms, alkoxy of 1 to 6 carbon atoms and nitro; and
A is hydrogen; or a salt thereof as therein defined.

3. A compound according to claim 1, wherein n is 6.

4. A compound according to claim 1 wherein $R_1$ is hydrogen or alkyl of 1 to 4 carbon atoms.

5. A compound according to claim 1 wherein $R_2$ is hydrogen, alkyl of 1 to 4 carbon atoms or phenyl.

6. A compound according to claim 1, wherein $R_3$ is hydroxy.

7. A compound according to claim 1 wherein $R_4$ is alkyl of 4 to 9 carbon atoms.

8. A compound according to claim 1 wherein $R_4$ is phenyl or a phenylalkyl wherein akyl has from 1 to 6 carbon atoms, said phenyl groups being unsubstituted or substituted by a member selected from the group consisting of halo, trifluoromethyl, alkyl of 1 to 6 carbon atoms, alkoxy of 1 to 6 carbon atoms and nitro.

9. A compound according to claim 1, wherein A is hydrogen.

10. A compound according to claim 1 wherein
n is 6;
$R_2$ is hydrogen, alkyl of 1 to 4 carbon atoms or phenyl;
$R_3$ is hydroxy; and
$R_4$ is hydrogen, alkyl of 1 to 9 carbon atoms, phenyl or phenylalkyl wherein alkyl has 1 to 6 carbon atoms, said phenyl groups being unsubstituted or substituted by a member selected from the group consisting of halo, trifluoromethyl, alkyl of 1 to 6 carbon atoms, alkoxy of 1 to 6 carbon atoms and nitro.

11. A compound according to claim 1 wherein
n is 6 or 8;
$R_1$ is hydrogen or alkyl of 1 to 4 carbon atoms;
$R_2$ is hydrogen, methyl or ethyl;
$R_3$ is hydroxy;
$R_4$ is hydrogen or alkyl of 1 to 9 carbon atoms; and
A is hydrogen; or a salt thereof as therein defined.

12. A compound according to claim 11 wherein n is 6.

13. A compound according to claim 11 wherein $R_2$ is methyl.

14. A compound according to claim 11 wherein $R_4$ is n-pentyl, n-hexyl or n-heptyl.

15. A compound according to claim 14 wherein $R_4$ is n-hexyl.

16. A compound according to claim 11 wherein $R_4$ is

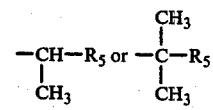

wherein $R_5$ is n-butyl, n-pentyl or n-hexyl.

17. A compound according to claim 11 wherein
n is 6;
$R_2$ is methyl;
$R_4$ is n-pentyl, n-hexyl, n-heptyl,

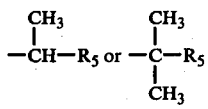

wherein R₅ is n-butyl, n-pentyl or n-hexyl; and
A is hydrogen.

18. A compound according to claim 1 wherein:
n is 6 or 8;
R₁ is hydrogen or alkyl of 1 to 4 carbon atoms;
R₃ is hydroxy;
R₂ is hydrogen, methyl or ethyl;
R₄ is a phenyl or phenylalkyl group of the formula

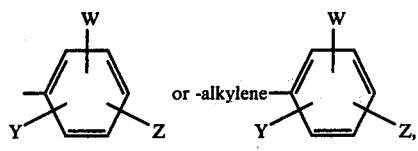

respectively, wherein alkylene contains from 1 to 6 carbon atoms and is straight chain or branched by one or two methyl groups at the same or different carbon atoms; and each of W, Y and Z is selected from the group consisting of hydrogen, fluoro, chloro, bromo, trifluoromethyl, methyl, ethyl, n-propyl, iso-propyl, methoxy, ethoxy, n-propoxy, iso-propoxy and nitro; and
A is hydrogen; or a salt thereof as therein defined.

19. A compound according to claim 18 wherein n is 6.
20. A compound according to claim 18 wherein R₂ is methyl.
21. A compound according to claim 18 wherein W and Y are hydrogen.
22. A compound according to claim 18 wherein R₄ is

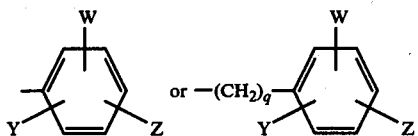

wherein q is 1 to 4.

23. A compound according to claim 18 wherein n is 6; R₂ is methyl; and W and Y are hydrogen.
24. A compound according to claim 23 wherein R₄ is

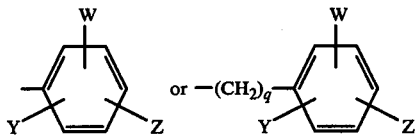

wherein q is 1 to 4.

25. A compound according to claim 1 wherein
n is 6 or 8;
R₁ is hydrogen or alkyl of 1 to 4 carbon atoms;
R₃ is hydroxy;
R₂ is hydrogen, methyl or ethyl;
R₄ is naphthyl or naphthylalkyl of the formula:

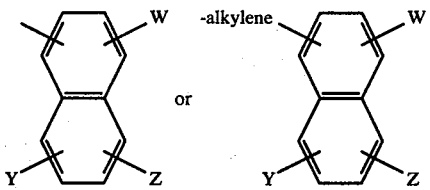

respectively, wherein alkylene contains from 1 to 6 carbon atoms and is straight chain or branched by one or two methyl groups at the same or different carbon atoms; and each of W, Y and Z is selected from the group consisting of hydrogen, fluoro, chloro, bromo, trifluoromethyl, methyl, ethyl, n-propyl, iso-propyl, methoxy, ethoxy, n-propoxy, iso-propoxy and nitro; and
A is hydrogen; or a salt thereof as therein defined.

26. A compound according to claim 25 wherein R₄ is

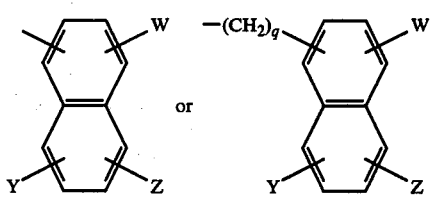

wherein q is 1 to 4.

27. A compound according to claim 1 wherein
n is 6 or 8;
R₁ is hydrogen or alkyl of 1 to 4 carbon atoms;
R₂ is phenyl;
R₄ is hydrogen or alkyl of 1 to 9 carbon atoms; and
A is hydrogen.

28. A compound according to claim 1 wherein
n is 6 or 8;
R₁ is hydrogen or alkyl of 1 to 4 carbon atoms;
R₂ is hydrogen, methyl or ethyl;
R₄ is hydrogen or alkyl of 1 to 9 carbon atoms; and A is methyl.

29. A compound according to claim 1 wherein
n is 6 or 8;
R₁ is hydrogen or alkyl of 1 to 4 carbon atoms;
R₃ is hydroxy;
R₂ is hydrogen or alkyl of 1 to 9 carbon atoms;
A is hydrogen, or methyl;
R₄ is a
cycloalkyl or cycloalkylalkyl group of the formula:

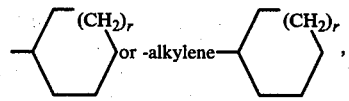

respectively, wherein r is 0 to 3; and alkylene contains from 1 to 6 carbon atoms and is straight chain or branched by one or two methyl groups at the same or different carbon atoms; or a salt thereof as therein defined.

30. A compound according to claim 29 wherein R₄ is

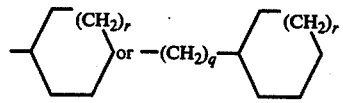

wherein q is 1 to 6 and r is 0 to 3.

31. A compound according to claim 1 wherein
n is 6 or 8;
$R_1$ is hydrogen or alkyl of 1 to 4 carbon atoms;
$R_3$ is hydroxy;
A is hydrogen or methyl; and
$R_2$ and $R_4$ taken together with the carbon atom to which they are joined are cycloalkyl of 5 to 8 carbon atoms; or a salt thereof as therein defined.

32. A pharmaceutical composition having as active agent an effective amount of a compound according to claim 1 to effect anti-gastric secretion activity, antihypertensive activity, bronchodilator activity and platelet aggregation inhibition activity and a pharmaceutically acceptable carrier.

33. The compound of claim 1 which is 4,4-dimethyl-2-(6'-ethoxycarbonyl-n-hexyl)-1-(3''-hydroxy-3''-methyl-n-nonyl)-pyrrolidin-3,5-dione.

34. The method of effecting antigastric secretion activity in humans and other animals which comprises administering thereto an effective amount of a compound according to claim 1.

35. The method of effecting antihypertensive activity in humans and other animals which comprises administering thereto an effective amount of a compound according to claim 1.

36. The method of effecting bronchodilator activity in humans and other animals which comprises administering thereto an effective amount of a compound according to claim 1.

37. The method of effecting platelet aggregation inhibition activity in humans and other animals which comprises administering thereto an effective amount of a compound according to claim 1.

* * * * *